(12) United States Patent
Wang et al.

(10) Patent No.: US 7,897,804 B2
(45) Date of Patent: Mar. 1, 2011

(54) PROCESSES FOR PREPARING ALKENYL ALKANOATES USING A LAYERED CATALYST COMPOSITION

(75) Inventors: Tao Wang, Houston, TX (US); Dean E. Rende, Des Plaines, IL (US); James E. Rekoske, Des Plaines, IL (US); Jeffery C. Bricker, Des Plaines, IL (US); Jeffrey L. Boike, Des Plaines, IL (US); Masao Takayama, Hiratsuka (JP); Kouji Hara, Hiratsuka (JP); Nobuyuki Aoi, Hiratsuka (JP)

(73) Assignee: Celanese International Corp., Dallas, TX (US)

( * ) Notice: Subject to any disclaimer, the term of this patent is extended or adjusted under 35 U.S.C. 154(b) by 0 days.

(21) Appl. No.: 12/098,951

(22) Filed: Apr. 7, 2008

(65) Prior Publication Data

US 2008/0287703 A1 Nov. 20, 2008

Related U.S. Application Data

(62) Division of application No. 11/137,180, filed on May 25, 2005.

(51) Int. Cl.
 *C07C 67/05* (2006.01)
(52) U.S. Cl. ..................................... 560/243
(58) Field of Classification Search ................. 560/243
 See application file for complete search history.

(56) References Cited

U.S. PATENT DOCUMENTS

| | | | |
|---|---|---|---|
| 3,441,601 A | 4/1969 | Sennewald et al. |
| 3,470,230 A | 9/1969 | Hirsch et al. |
| 3,775,342 A | 11/1973 | Kronig et al. |
| 3,822,308 A | 7/1974 | Kronig et al. |
| 4,087,622 A | 5/1978 | Nakamura et al. |
| 4,340,504 A | 7/1982 | Courty et al. |
| 4,420,420 A | 12/1983 | Mita et al. |
| 4,764,498 A | 8/1988 | Wissner et al. |
| 4,902,823 A | 2/1990 | Wunder et al. |
| 4,977,126 A | 12/1990 | Mauldin et al. |
| 5,185,308 A | 2/1993 | Bartley et al. |
| 5,194,417 A | 3/1993 | Smith et al. |
| 5,200,382 A | 4/1993 | Cody et al. |
| 5,274,181 A | 12/1993 | Bartley et al. |
| 5,314,858 A | 5/1994 | Colling |
| 5,332,710 A | 7/1994 | Nicolau et al. |
| 5,336,802 A | 8/1994 | Smith et al. |
| 5,342,987 A | 8/1994 | Bartley |
| 5,466,652 A | 11/1995 | Paparizos et al. |
| 5,559,071 A | 9/1996 | Abel et al. |
| 5,567,839 A | 10/1996 | Gulliver et al. |
| 5,576,457 A | 11/1996 | Abel |
| 5,691,267 A | 11/1997 | Nicolau et al. |
| 5,700,753 A | 12/1997 | Wang et al. |
| 5,808,136 A | 9/1998 | Tacke et al. |
| 5,859,287 A | 1/1999 | Nicolau et al. |
| 5,935,889 A | 8/1999 | Murrell et al. |
| 5,990,344 A | 11/1999 | Couves et al. |
| 6,015,769 A | 1/2000 | Wang |
| 6,017,847 A | 1/2000 | Wang |
| 6,022,823 A | 2/2000 | Augustine et al. |
| 6,034,030 A | 3/2000 | Nicolau et al. |
| 6,057,260 A | 5/2000 | Nicolau et al. |
| 6,107,513 A | 8/2000 | Herzog et al. |
| 6,107,514 A | 8/2000 | Nicolau et al. |
| 6,114,571 A | 9/2000 | Abel et al. |
| 6,114,573 A | 9/2000 | Herzog |
| 6,143,921 A | 11/2000 | Karim et al. |
| 6,156,927 A | 12/2000 | Halcom et al. |
| 6,225,496 B1 | 5/2001 | Baker et al. |
| 6,258,978 B1 | 7/2001 | Kitchen et al. |
| 6,268,522 B1 | 7/2001 | Hagemeyer et al. |
| 6,280,608 B1 * | 8/2001 | Jensen et al. ................. 208/143 |
| 6,303,537 B1 | 10/2001 | Wang et al. |
| 6,342,628 B1 | 1/2002 | Williams et al. |
| 6,346,501 B1 | 2/2002 | Herzog et al. |

(Continued)

FOREIGN PATENT DOCUMENTS

CA 820352 8/1969

(Continued)

OTHER PUBLICATIONS

Search Report for PCT/US2006/012064, dated Aug. 11, 2006.

*Primary Examiner*—Deborah D Carr
(74) *Attorney, Agent, or Firm*—Simmons Perrine Moyer Bergman PLC

(57) ABSTRACT

A layered composition which can be used in various processes has been developed. The composition comprises an inner core such as a cordierite core and an outer layer comprising a refractory inorganic oxide, a fibrous component and an inorganic binder. The refractory inorganic oxide layer can be alumina, zirconia, titania, etc. while the fibrous component can be titania fibers, silica fibers, carbon fibers, etc. The inorganic oxide binder can be alumina, silica, zirconia, etc. The layer can also contain catalytic metals such as gold and platinum plus other modifiers. The layered composition is prepared by coating the inner core with a slurry comprising the refractory inorganic oxide, fibrous component, an inorganic binder precursor and an organic binding agent such as polyvinyl alcohol. The composition can be used in various hydrocarbon conversion processes including production of vinyl acetate.

23 Claims, No Drawings

U.S. PATENT DOCUMENTS

| | | |
|---|---|---|
| 6,350,900 B1 | 2/2002 | Wang et al. |
| 6,350,901 B1 | 2/2002 | Kitchen et al. |
| 6,358,882 B1 | 3/2002 | Salem et al. |
| 6,376,706 B2 | 4/2002 | Kitchen et al. |
| 6,399,813 B1 | 6/2002 | Blum et al. |
| 6,407,283 B2 | 6/2002 | Couves et al. |
| 6,420,308 B1 | 7/2002 | Khanmamedova |
| 6,448,432 B2 | 9/2002 | Williams |
| 6,472,556 B2 | 10/2002 | Kitchen et al. |
| 6,486,093 B2 | 11/2002 | Wang et al. |
| 6,486,370 B1 | 11/2002 | Rende et al. |
| 6,492,299 B1 | 12/2002 | Couves et al. |
| 6,603,038 B1 | 8/2003 | Hagemeyer et al. |
| 6,849,243 B1 * | 2/2005 | Hagemeyer et al. ......... 423/344 |
| 2001/0048970 A1 | 12/2001 | Hagemeyer et al. |
| 2002/0013220 A1 | 1/2002 | Wang et al. |
| 2002/0016495 A1 | 2/2002 | Williams |
| 2002/0058833 A1 | 5/2002 | Cirjak et al. |
| 2002/0188152 A1 | 12/2002 | Khanmamedova |
| 2002/0198404 A1 | 12/2002 | Herzog et al. |
| 2003/0059356 A1 | 3/2003 | Hoke et al. |
| 2003/0109746 A1 | 6/2003 | Fiorentino et al. |
| 2003/0148883 A1 | 8/2003 | Khanmamedova et al. |
| 2003/0161775 A1 | 8/2003 | Rodemerck et al. |
| 2003/0166466 A1 | 9/2003 | Hoke et al. |
| 2006/0091580 A1 * | 5/2006 | Mulligan et al. ....... 264/172.15 |
| 2006/0266673 A1 | 11/2006 | Rende et al. |

FOREIGN PATENT DOCUMENTS

| | | |
|---|---|---|
| DE | 19914066 A1 | 10/2000 |
| DE | 10030039 A1 | 1/2002 |
| EP | 0347830 A2 | 6/1989 |
| EP | 0569624 | 11/1993 |
| EP | 0634208 | 7/1994 |
| EP | 0634209 | 7/1994 |
| EP | 0654301 | 5/1995 |
| EP | 0672453 | 9/1995 |
| EP | 0685449 | 12/1995 |
| EP | 0685451 | 12/1995 |
| EP | 0871604 | 5/1996 |
| EP | 0891226 | 3/1997 |
| EP | 0847982 | 6/1998 |
| EP | 0997192 | 9/1998 |
| EP | 0891224 | 1/1999 |
| EP | 0898494 | 3/1999 |
| EP | 1015108 | 6/2001 |
| EP | 0723810 | 7/2001 |
| EP | 0906151 | 7/2001 |
| EP | 0874798 | 8/2001 |
| EP | 0986433 | 8/2001 |
| EP | 0877727 | 11/2001 |
| EP | 0909213 | 11/2001 |
| EP | 1164123 | 12/2001 |
| EP | 0827422 | 2/2002 |
| EP | 0839793 | 3/2002 |
| EP | 1230977 | 8/2002 |
| EP | 1102635 | 10/2002 |
| EP | 1106247 | 3/2003 |
| EP | 1323469 | 7/2003 |
| JP | 10081508 | 3/1998 |
| JP | 10139727 | 5/1998 |
| JP | 10195021 | 7/1998 |
| JP | 10328571 | 12/1998 |
| JP | 11009997 | 1/1999 |
| JP | 11244696 | 9/1999 |
| JP | 11244697 | 9/1999 |
| JP | 11268017 | 10/1999 |
| JP | 11349534 | 12/1999 |
| JP | 2000169430 | 12/1999 |
| JP | 2000000473 | 1/2000 |
| JP | 2000063324 | 2/2000 |
| JP | 2000063325 | 2/2000 |
| JP | 2000063326 | 2/2000 |
| JP | 2000086335 | 3/2000 |
| JP | 2000119219 | 4/2000 |
| JP | 2000176285 | 6/2000 |
| JP | 2000218152 | 8/2000 |
| JP | 2002030036 | 6/2001 |
| WO | WO 94/21374 | 9/1994 |
| WO | WO 97/33690 | 9/1997 |
| WO | WO 97/36678 | 10/1997 |
| WO | WO 97/36679 | 10/1997 |
| WO | WO 97/37759 | 10/1997 |
| WO | WO 97/38790 | 10/1997 |
| WO | WO 97/44130 | 11/1997 |
| WO | WO 98/00232 | 1/1998 |
| WO | WO 98/05620 | 2/1998 |
| WO | WO 98/52688 | 11/1998 |
| WO | WO 98/55225 | 12/1998 |
| WO | WO 98/55443 | 12/1998 |
| WO | WO 99/08790 | 2/1999 |
| WO | WO 99/21650 | 5/1999 |
| WO | WO 99/22863 | 5/1999 |
| WO | WO 99/29418 | 6/1999 |
| WO | WO 99/29419 | 6/1999 |
| WO | WO 99/30818 | 6/1999 |
| WO | WO 99/39824 | 8/1999 |
| WO | WO 99/42212 | 8/1999 |
| WO | WO 99/51339 | 10/1999 |
| WO | WO 99/62632 | 12/1999 |
| WO | WO 99/62633 | 12/1999 |
| WO | WO 99/62634 | 12/1999 |
| WO | WO 00/07727 | 2/2000 |
| WO | WO 01/07496 | 6/2000 |
| WO | WO 00/44496 | 8/2000 |
| WO | WO 00/51962 | 9/2000 |
| WO | WO 00/58008 | 10/2000 |
| WO | WO 00/66261 | 11/2000 |
| WO | WO 00/69802 | 11/2000 |
| WO | WO 01/00559 | 1/2001 |
| WO | WO 01/36091 | 5/2001 |
| WO | WO 01/36092 | 5/2001 |
| WO | WO 01/90042 | 11/2001 |
| WO | WO 01/90043 | 11/2001 |
| WO | WO 02/04392 | 1/2002 |

* cited by examiner

US 7,897,804 B2

PROCESSES FOR PREPARING ALKENYL ALKANOATES USING A LAYERED CATALYST COMPOSITION

CLAIM OF PRIORITY

This application is a divisional of U.S. patent application Ser. No. 11/137,180, filed on May 25, 2005, which is hereby incorporated by reference.

FIELD OF THE INVENTION

This invention relates to a layered composition, a process for preparing and a hydrocarbon conversion process using the composition. The composition comprises an inner core such as cordierite and an outer layer comprising an outer refractory inorganic oxide and a fibrous component. The outer layer can optionally comprise a catalytic component dispersed thereon.

BACKGROUND OF THE INVENTION

Numerous commercial processes are carried out using a catalyst. This is especially true of various hydrocarbon conversion processes. These catalysts comprise one or more catalytic element deposited onto a relatively high surface area support. Further, the catalytic element or component can be evenly dispersed throughout the support, be dispersed on the surface of the support or present as a band below the surface.

The art also discloses catalysts containing an inert core or layer and an active outer layer or shell. For example, U.S. Pat. No. 3,145,183 discloses spheres having an impervious center and a porous shell. Although it is disclosed that the impervious center can be small, the overall diameter is 1/8" or larger. It is stated that for smaller diameter spheres (less than 1/8"), uniformity is hard to control. U.S. Pat. No. 5,516,740 discloses a thin outer shell of catalytic material bonded to an inner core of catalytically inert material. The outer layer can have catalytic metals such as platinum dispersed on it. The '740 patent further discloses that this catalyst is used in an isomerization process. Finally, the outer layer material contains the catalytic metal prior to it being coated onto the inner core.

U.S. Pat. No. 4,077,912 and U.S. Pat. No. 4,255,253 disclose a catalyst having a base support having deposited thereon a layer of a catalytic metal oxide or a combination of a catalytic metal oxide and an oxide support. U.S. Pat. No. 5,935,889 discloses a catalyst which comprises a catalytically inert core material on which is deposited and bonded a thin shell of material containing active sites. Finally, U.S. Pat. No. 6,177,381 discloses a layered catalyst composition containing an inner core, an outer layer bonded to the inner core and where the outer layer has dispersed thereon a platinum group metal, a promoter metal and a modifier metal.

One problem associated with the layered compositions of the prior art is that the strength or attrition resistance was not sufficient for certain applications. Applicants have discovered that adding a fibrous component to the outer layer greatly increases its strength. The fibrous components can be either inorganic fibers such as silica or mullite fibers or organic fibers such as carbon fibers.

SUMMARY OF THE INVENTION

One embodiment of the invention is a layered composition comprising an inner core and an outer layer comprising a refractory inorganic oxide and a fibrous component.

Another embodiment of the invention is a process for preparing the layered composition described above, the process comprising coating an inner core with a slurry comprising the outer refractory inorganic oxide, a fibrous component, an inorganic binder, an organic bonding agent and a solvent to give a coated core; and calcining the coated core at a temperature of at least 200° C. for a time sufficient to bond the outer layer to the inner core and provide a layered composition.

Yet another embodiment of the invention is a hydrocarbon conversion process comprising contacting a hydrocarbon with the layered composition described above at conversion conditions to give a converted product.

These and other objects and embodiments will become clearer after a detailed description of the invention.

DETAILED DESCRIPTION OF THE INVENTION

One element of the layered composition of the present invention is an inner core. One characteristic of the materials which can be used for the inner core is the ability to be formed into a desired shape. Examples of materials which can be used include but are not limited to metals, refractory inorganic oxides and silicon carbide. Refractory inorganic oxides are preferred with non-limiting examples being aluminas, cordierite, mullite, montmorillonite, silica, zirconia, titania and mixtures thereof. Aluminas include gamma, theta, delta and alpha alumina. A preferred inorganic oxide is cordierite. When the inner core is a refractory inorganic oxide, it is necessary that it be different from the outer layer refractory inorganic oxide.

Further, when the outer layer will have additional components, e.g. metals or metal oxides, which are deposited thereon by impregnation means, it is preferred that the inner core have a lower adsorptive capacity relative to the outer layer. This adsorptive capacity is with respect to solvents which may be used to impregnate the outer layer with a compound of a catalytic component. The inner core should also have a substantially lower capacity for the compounds themselves versus the outer layer.

These materials which form the inner core can be formed into a variety of shapes such as pellets, extrudates, spheres, hollow tubes or irregularly shaped particles although not all materials can be formed into each shape. Preparation of the inner core can be done by means known in the art such as oil dropping, pressure molding, metal forming, pelletizing, granulation, extrusion, rolling methods and marumerizing. A spherical inner core is preferred. The inner core whether spherical or not has an effective average diameter of about 0.05 mm to about 15 mm and preferably from about 0.5 mm to about 10 mm. For a non-spherical inner core, effective diameter is defined as the diameter the shaped article would have if it were molded into a sphere. Once the shaped inner core is formed it is optionally calcined at a temperature of about 400° C. to about 1500° C.

The inner core is now coated with a layer of a refractory inorganic oxide which is different from the inorganic oxide which may be used as the inner core and will be referred to as the outer refractory inorganic oxide. This outer refractory oxide is one which has good porosity, has a surface area of at least 2 m²/g, and preferably at least 20 m²/g and most preferably at least 30 m²/g, an apparent bulk density of about 0.2 g/ml to about 1.8 g/ml. Non-limiting examples of the refractory inorganic oxides which can be used are gamma alumina, delta alumina, eta alumina, theta alumina, silica/alumina, zeolites, non-zeolitic molecular sieves (NZMS), titania, zirconia and mixtures thereof. It should be pointed out that silica/alumina is not a physical mixture of silica and alumina but means an acidic and amorphous material that has been cogelled or coprecipitated. This term is well known in the art, see e.g., U.S. Pat. No. 3,909,450, U.S. Pat. No. 3,274,124 and U.S. Pat. No. 4,988,659, all of which are incorporated by reference. Examples of zeolites include, but are not limited to, zeolite Y, zeolite X, zeolite L, zeolite beta, ferrierite, MFI, UZM-4 (see U.S. Pat. No. 6,776,975), UFI, UZM-8 (U.S. Pat. No. 6,756,030), UZM-9 (U.S. Pat. No. 6,713,041), mordenite and erionite. Non-zeolitic molecular sieves (NZMS) are those molecular sieves which contain elements other than aluminum and silicon and include silicoaluminophosphates (SAPOs) described in U.S. Pat. No. 4,440,871, ELAPOs described in U.S. Pat. No. 4,793,984, MeAPOs described in U.S. Pat. No. 4,567,029 all of which are incorporated by reference. Preferred refractory inorganic oxides are gamma, eta alumina and zirconia.

The refractory inorganic oxide is applied to the inner core by first forming a slurry comprising the refractory inorganic oxide. The slurry is formed by admixing a solvent with the refractory inorganic oxide to form a mixture and milling the mixture for a time sufficient to form a slurry. The solvent which is usually used is water although organic solvents can also be used. The mixture can also contain an agent which will aid in forming the slurry such as but not limited to nitric acid, hydrochloric acid, sulfuric acid and acetic acid. The slurry will also contain an inorganic binder precursor which is usually, a sol, a gel or a compound of a metal which on heating will decompose to form an inorganic oxide binder. The inorganic binders which can be used include but are not limited to alumina, silica, zirconia, titania, aluminum phosphate, etc. Nonlimiting examples of binder precursors which can be added to the slurry are: $ZrO(C_2H_3O_2)_2$; $ZrO(NO_3)_2$; $ZrO(OH)Cl \cdot nH_2O$; zirconia sol; $ZrOCO_3$; $ZrO(OH)_2$; $Zr(C_5H_8O_2)_4$; $Zr(SO_4)_2 \cdot 4H_2O$; alumina sol; silica sol; aluminum nitrate and boehmite. Although in some cases it is preferred that the binder give the same refractory oxide as the outer layer oxide, generally any inorganic binder can be used with any outer layer refractory oxide. For example, an alumina binder can be used when the outer layer is a zeolite, titania, silica or alumina. However, it has been found that when zirconia is the outer refractory inorganic layer, it is preferred to have a zirconia binder. The amount of inorganic binder precursor present in the slurry is that amount which will provide from about 1 wt. % to about 99 wt. % inorganic binder on the deposited outer layer. Preferably the amount of binder precursor present is that amount which will give from 2 to 40 wt. % of the outer layer of inorganic binder and most preferably the amount which will provide from 5 to 30 wt. % of the outer layer.

Another necessary component of the slurry is a fibrous component. Suitable fibrous components include those that comprise fibers that are elongated, thread-like objects or structures or filaments. The types of fibers which can be used include both inorganic and organic fibers either of which can be natural or synthetic. Generally fibers can comprise a large array of materials including without limitation glasses, minerals, metal oxides, ceramics, metals, polymers and carbons. Specific examples of inorganic fibers include but are not limited to titania fibers, potassium titanate fibers, zirconia fibers, mullite fibers, alumina fibers, silicon carbide fibers, glass wool, boron fibers, aluminum fibers, silica fibers and cordierite fibers. A preferred fiber which is mostly silica (60% $SiO_2$, 33% CaO and 6% MgO) is Superwool™ manufactured and sold by Thermal Ceramics. Nonlimiting examples of organic fibers are graphite fibers, carbon fibers and polymeric fibers such as polyethylenes, polyesters, polyurethanes, polyamides, aromatic polyamides (e.g. Kevlar™), polystyrenes (e.g. syndiotactic polystyrene), polytetrafluoroethylenes (e.g. Teflon™). Furthermore, combinations of materials may be used in the fibers as well as combinations of fibers in the fibrous component. It should be pointed out that when organic fibers are used, the subsequent treating temperatures and the process temperature that it will be used at must be below the combustion temperature of the organic fibers. Obviously the inorganic fibers will not combust, but the operating temperature must be below its melting temperature. Furthermore, fibers may be further treated (e.g. coated) to accentuate desirable characteristics (e.g. treated to increase decomposition or melting temperature). While the fibrous component may include fibers that are woven, braided or otherwise entangled or connected in an unwoven manner, the fibers may also be free of connections with other fibers.

Although the length of the fibers is not critical, usually the fibers have a length from about 1 to about 10,000 micrometers, preferably from about 2 to about 1,000 micrometers and most preferably from about 5 to about 300 micrometers. The fibers also have varying diameters which again is not critical. Smaller diameter fibers are more easily dispersed and thus are preferred. Since both the length and diameter of the fibers can be varied, a preferred length/diameter (L/D) ratio can be determined experimentally. This L/D ratio is different for different fibers.

The amount of fibers which can be added to the slurry can vary considerably and is usually that amount which will give from about 1 to about 30 wt. % of the final layer weight, preferably from about 1 to about 20 wt. % and most preferably from about 3 to about 10 wt. %.

It is also necessary that the slurry contain an organic bonding agent which aids in the adhesion of the layer material to the inner core. Examples of this organic bonding agent include but are not limited to polyvinyl alcohol (PVA), hydroxy propyl cellulose, methylcellulose and carboxy methylcellulose. The amount of organic bonding agent which is added to the slurry will vary considerably from about 0.1 wt. % to about 5 wt. % of the slurry.

As stated, the slurry is milled using any of a variety of mills known in the art such as ball milling, impact milling, etc. Milling is carried out to ensure adequate blending of the various components and to optionally reduce the particle size of the refractory inorganic oxide powder and/or fibers. Milling is usually carried out for a time of about 2 to about 8 hours.

Coating of the inner core with the slurry can be accomplished by means such as rolling, dipping, spraying, etc. One preferred technique involves using a fixed fluidized bed of inner core particles and spraying the slurry into the bed to coat the particles evenly. The thickness of the layer can vary considerably, but usually is from about 40 to about 400 micrometers preferably from about 40 to about 300 micrometers and most preferably from about 50 to about 200 micrometers. It should be pointed out that the optimum layer thickness depends on the use for the catalyst and the choice of the outer refractory oxide. Once the inner core is coated with the layer of outer refractory inorganic oxide, the resultant layered composition is dried at a temperature of about 100° C. to about 150° C. for a time of about 1 to about 24 hours and then calcined at a temperature of at least 200° C. for a time of about 0.5 to about 10 hours to effectively bond the outer layer to the inner core and provide a layered composition. The calcination conditions are chosen to not only effectively bond the outer layer to the inner core but to optimize the characteristics of the outer layer, e.g. surface area of the layer, integrity of the fibers, pore volume of the inorganic oxide etc. As stated above, if organic fibers are used the calcination temperature must be below their combustion temperature. Thus, preferred calcination temperatures are from about 200° C. to about 1500° C. and most preferably from about 400° C. to about 1100° C. Finally, the drying and calcining steps can be combined into one step. It should also be pointed out that in some cases it may be necessary to carry out the layering process more than once in order to obtain the desired layer thickness. Intermediate calcining steps may not be necessary with a drying step being sufficient to ensure that the first layer does not dissolve during the subsequent layering step.

In one embodiment of the invention, the layered composition comprises more than one layer. Successive layers are applied to the coated composition after the first (or subsequent layer) has been calcined. Coating of a layered core is carried out as described above for the first layer. The second layer of refractory inorganic oxide is different from the first layer and will be different from the third layer (if any), although the first and third layer can be the same inorganic oxide. Thus, it is only necessary that adjacent layers be of different refractory inorganic oxides. The thickness of each layer is as stated for the first layer and the number of additional layers can vary from 1 to about 5 layers or more.

As stated the use of fibers in the outer layer greatly improves the strength or attrition resistance of the resultant layered composition. The strength of the layered composition was determined by measuring its impact breakage (IB). Impact breakage was determined by taking an amount of layered composition (about 50 cc) after calcination, placing them in a flat drum and rotating the drum at 25 rpm for 10 minutes. The fines were collected, weighted and the IB determined from the following equation:

$$IB = (\text{Weight of Fines/Total Weight of Layered Composition}) \times 100\%$$

The layered composition of the invention will have an IB of preferably less than about 10 wt. %, more preferably less than about 5 wt. % and most preferably less than about 3 wt. %. Ranges within the above stated ranges are also contemplated.

Although the layered composition described above can be used as is to catalyze various reactions, it is usually used as a support for various catalytic components. These catalytic components are selected from the group consisting of Groups 3-12 of the Periodic Table of the Elements using the IUPAC system of numbering the groups and as set forth at http://pearl1.lanl.gov/periodic/default.htm. Preferred catalytic elements or metals are the noble metals or platinum group metals which include platinum, palladium, rhodium, ruthenium, osmium and iridium. Gold and silver are also preferred catalytic metals. Combinations of catalytic components are also preferred, such as palladium used in combination with gold and/or rhodium.

These catalytic metal components can be deposited on the layered support in any suitable manner known in the art. One method involves impregnating the layered composition or support with a solution (usually aqueous, although organic solvents can be used) of a decomposable compound of the catalytic metal or metals. By decomposable is meant that upon heating the metal compound is converted to the metal or metal oxide with the release of byproducts. Examples of the compounds which can be used include without limitation chlorides, other halides, nitrates, nitrites, hydroxides, oxides, oxalates, acetates, sulfates and amines. Illustrative examples of decomposable compounds of the platinum group metals are chloroplatinic acid, ammonium chloroplatinate, bromoplatinic acid, dinitrodiamino platinum, sodium tetranitroplatinate, rhodium trichloride, hexaamminerhodium chloride, rhodium carbonylchloride, sodium hexanitrorhodate, chloropalladic acid, palladium chloride, palladium nitrate, diamminepalladium hydroxide, tetraamminepalladium chloride, hexachloroiridate (IV) acid, hexachloroiridate (III) acid, ammonium hexachloroiridate (III), ammonium aquohexachloroiridate (IV), ruthenium tetrachloride, hexachlororuthenate, hexaammineruthenium chloride, osmium trichloride and ammonium osmium chloride. Examples of other palladium compounds include but are not limited to $Na_2PdCl_4$, $Pd(NH_3)_4(NO_2)_2$, $Pd(NH_3)_4(OH)_2$, $Pd(NH_3)_4(NO_3)_2$, $Pd(NH_3)_4(OAc)_2$, $Pd(NH_3)_2(OAc)_2$, $Pd(OAc)_2$ in KOH and/or $NMe_4OH$ and/or NaOH, $Pd(NH_3)_4(HCO_3)_2$ and palladium oxalate. Examples of gold and silver compounds include but are not limited to $AuCl_3$, $HAuCl_4$, $NaAuCl_4$, $KAuO_2$, $NaAuO_2$, $NMe_4AuO_2$, $Au(OAc)_3$, $HAu(NO_3)_4$, $AgNO_3$, $AgC_2H_3O_2$ and $AgClO_3$. Solubility modifiers may be utilized to aid in solubilizing the decomposable compound of the catalytic metal or metals. For example, acids or bases may be used to facilitate the catalytic compound going into solution. In one embodiment, KOH and/or $NMe_4OH$ is used in combination with $Au(OAc)_3$ or nitric acid is used with $HAu(NO_3)_4$.

Multiple solutions containing the catalytic compounds may be impregnated onto the layered composition or support simultaneously (e.g. co-impregnation) or sequentially and may be impregnated through the use of one or multiple solutions.

One or more calcining steps may be used, such that at any point after at least one catalytic component compound is contacted with the layered composition or refractory inorganic oxide, it may be calcined. For example, the calcining step is carried out at a temperature in the range of about 100° C. to about 700° C., preferably between about 200° C. and about 500° C. in a non-reducing atmosphere. Calcination times may vary but preferably are between about 1 and 5 hours. The degree of decomposition of the catalytic component compound depends on the temperature used and length of time the impregnated catalyst is calcined and can be followed by monitoring volatile decomposition products.

Preferably, the last calcining step occurs before contact of the gold catalytic component to a zirconia containing layered composition. Alternately, calcining of a zirconia containing support composition containing gold is conducted at temperatures below about 300° C. Exemplary protocols including a calcining step include: a) impregnating with palladium followed by calcining followed by impregnating with gold; b) co-impregnating palladium and rhodium followed by calcining followed by impregnating with gold; c) impregnating with palladium followed by calcining followed by impregnating with rhodium followed by calcining followed by impregnating with gold; or d) impregnating with palladium and rhodium, followed by impregnating with gold, followed by calcination.

One impregnation procedure involves the use of a steam-jacketed rotary dryer. The layered composition is immersed in the impregnating solution containing the desired metal compound(s) contained in the dryer and the support is tumbled therein by the rotating motion of the dryer. Evaporation of the solution in contact with the tumbling support is expedited by applying steam to the dryer jacket. The resultant composite is allowed to dry under ambient temperature conditions, or dried at a temperature of about 80° to about 110° C., followed by calcination, thereby converting the metal compound to the metal or metal oxide.

Another impregnation procedure is spray impregnation which is well known in the art and is presented here only for completeness. The layered composition is loaded into a drum and a spray nozzle is inserted into the opening of the drum.

The support is tumbled and the metal containing solution is delivered through the spray nozzle for 15 to 30 minutes. The amount of solution can be varied to determine the depth of penetration into the support. The support is dried at 110° C. to 150° C. and additional metals can be added by repeating the above procedure or the support can be calcined to convert the metal compounds to the metal or metal oxide.

The dispersion of the catalytic metals can either be done as described above after the refractory inorganic oxide has been applied to the inner core or the refractory inorganic oxide can first be impregnated with the desired solution, dried, calcined, slurried and then applied to the inner core. If the layered composition contains more than one layer, all the layers need not have catalytic metals dispersed thereon. For example, the first layer can have one or more catalytic metal dispersed thereon, while the second layer does not have any catalytic metals thereon or vice versa. Alternatively, the first layer can have one or more catalytic metal while the second layer has different catalytic metal(s).

In addition to the catalytic components, various promoters and modifiers can also be dispersed on the layered composition. Promoters and modifiers can be any elements selected from the group consisting of alkali metals, alkaline earth metals, tin, germanium, rhenium, gallium, bismuth, lead, indium, cerium, zinc, boron and mixtures thereof. One preferred promoter for use in vinyl acetate production is an alkali metal, which may be provided in the form of an acetate such as KOAc. The addition of the alkali metal may be referred to as activating the catalyst.

The promoter and modifier components can be dispersed onto the layered support in the same way as described for the catalytic component. All the components can be impregnated using one common solution or they can be sequentially impregnated in any order, but not necessarily with equivalent results. Additionally, these promoters and modifiers can be present in one layer, but not in another layer. They can also be present in a layer where there are no catalytic metals or only in layers where there are catalytic metals.

When it is stated that the catalytic components, promoters and modifiers are "dispersed or deposited on" the outer layer it is meant that they can be dispersed either on the surface of the layer, throughout the layer or even below the outer surface in a tight band. It should be pointed out that when the inner core comprises a material that has some adsorptive property, a small fraction of the catalytic component, promoter and/or modifier can be found on or throughout the core.

The catalysts of the present invention may be utilized to produce alkenyl alkanoates from an alkene, alkanoic acid and an oxygen containing gas in the presence of a catalyst. Preferred alkene starting materials contain from two to four carbon atoms (e.g. ethylene, propylene and n-butene). Preferred alkanoic acid starting materials used in the process of this invention for producing alkenyl alkanoates contain from two to four carbon atoms (e.g., acetic, propionic and butyric acid). Preferred products of the process are vinyl acetate, vinyl propionate, vinyl butyrate, and allyl acetate. The most preferred starting materials are ethylene and acetic acid with the vinyl acetate being the most preferred product. Thus, the present invention is useful in the production of olefinically unsaturated carboxylic esters from an olefinically unsaturated compound, a carboxylic acid and oxygen in the presence of a catalyst. Other methods of making alkenyl alkanoates may be found in U.S. application Ser. No. 10/993,507, which incorporated by reference.

When vinyl acetate is produced using the catalyst of the present invention, a stream of gas, which contains ethylene, oxygen or air, and acetic acid is passed over the catalyst. The composition of the gas stream can be varied within wide limits, taking into account the zone of flammability of the effluent. For example, the molar ratio of ethylene to oxygen can be about 80:20 to about 98:2, the molar ratio of acetic acid to ethylene can be about 100:1 to about 1:100, preferably about 10:1 to 1:10, and most preferably about 1:1 to about 1:8. The gas stream may also contain gaseous alkali metal acetate and/or inert gases, such as nitrogen, carbon dioxide and/or saturated hydrocarbons. Reaction temperatures which can be used are elevated temperatures, preferably those in the range of about 125-220° C. The pressure employed can be a somewhat reduced pressure, normal pressure or elevated pressure, preferably a pressure of up to about 2026 kPa (20 atmospheres gauge).

For a vinyl acetate catalyst according to the present invention preferably comprises between about 1 to about 10 grams of palladium, and about 0.5 to about 10 grams of gold per liter of catalyst. The amount of gold is preferably from about 10 to about 125 wt % based on the weight of palladium. Further, the catalyst preferably contains about 10 to about 70, preferably about 20 to about 60 grams of promoter (e.g. KOAc) per liter of catalyst.

In one application, a layered catalytic composite is used to produce vinyl acetate from the reaction of ethylene with acetic acid and oxygen. In this particular case, the inner core preferably comprises cordierite and the refractory oxide layer is a zirconia layer having fibers such as mullite, Superwool or $TiO_2$. The layered composition has dispersed thereon palladium, gold and potassium with rhodium being optional. A preferred method of dispersing the metals onto the support is to first impregnate the layered support with an aqueous solution comprising a palladium compound such as $Pd(NH_3)_4(OH)_2$ and then calcining the impregnated layered composition. Next the calcined composition is impregnated with a solution comprising a gold compound such as $KAuO_2$, drying, calcining, and finally reducing the catalyst at a temperature from ambient to about 550° C. for a time of about 1 to about 5 hours. Reduction is carried out under hydrogen or other reducing atmospheres. Addition of a promoter may be carried out before or after the reduction step.

The layered composition of the invention with catalytic metals thereon can also be used for other hydrocarbon conversion processes such as hydrocracking, cracking, isomerization, hydrogenation, dehydrogenation, oxidation and alkylation of both aromatic and isoparaffin hydrocarbons. The desirable catalytic metals for these reactions are the platinum group metals, as described above. Promoter metals selected from the group consisting of Sn, Ge, Re, Ga, Bi, Pb, In, Ce, Zn and mixtures thereof can also be present as well as modifier metals selected from the group consisting of alkali metals, alkaline earth metals and mixtures thereof can also be dispersed on the layered support. Methods of dispersing these various components onto the layered support are as set forth above. As described in U.S. Pat. No. 6,280,608 B1 and incorporated herein by reference in its entirety, a halogen component can also be present on the layered catalytic component.

Although in the above embodiments all three metals are uniformly dispersed in the outer layer of refractory oxide and substantially present only in the outer layer, it is also within the bounds of this invention that the modifier metal can be present both in the outer layer and the inner core. This is owing to the fact that the modifier metal can migrate to the inner core, when the core is other than a metallic core.

Although the concentration of each metal component can vary substantially, it is desirable that the platinum group metal be present in a concentration of about 0.01 to about 5 weight percent on an elemental basis of the entire weight of the catalytic composition and preferably from about 0.05 to about 2.0 wt. %. The promoter metal is present in an amount from about 0.05 to about 10 wt. % of the entire catalytic composition while the modifier metal is present in an amount from about 0.1 to about 5 wt. % and preferably from about 2 to about 4 wt. % of the entire catalytic composition.

The conditions necessary to carry out alkylation of aromatic compounds are well known and are disclosed, for example, in U.S. Pat. No. 3,965,043 and U.S. Pat. No. 3,979,331 which are incorporated by reference. Generally the process can be carried out in a batch type or a continuous type operation. In a batch type process, the catalyst, aromatic compound and alkylating agent are placed in an autoclave and the pressure increased, if necessary, in order to effect the reaction in the liquid phase. An excess amount of aromatic compound should be present, preferably in a range of about 2:1 to about 20:1 moles of aromatic compound per mole of alkylating agent. The reaction is carried out at an elevated temperature since the rate of alkylation is undesirably low at room temperature. Preferably the temperature is in the range of about 40° C. to about 200° C. The process is carried out for a time of about 0.5 to about 4 hours, after which the product is separated from the starting materials by conventional means.

If it is desired to carry out the process in a continuous manner, the catalyst is placed in a reactor which is heated to the desired operating temperature and the pressure increased above atmospheric, if necessary. The aromatic compound and alkylating agent are flowed over the catalyst bed at a predetermined liquid hourly space velocity sufficient to effect alkylation. The effluent is continuously withdrawn and conventional separation means used to isolate the desired product.

Hydrocracking conditions typically include a temperature in the range of 240° C. to 649° C. (400° F.-1200° F.), preferably between about 316° C. and about 510° C. (600-950° F.). Reaction pressures are in the range of atmospheric to about 24,132 kPag (3,500 psig), preferably between about 1,379 and 20,685 kPag (200-3,000 psig). Contact times usually correspond to liquid hourly space velocities (LHSV) in the range of about 0.1 $hr^{-1}$ to 15 $hr^{-1}$, preferably between about 0.2 and 3 $hr^{-1}$. Hydrogen circulation rates are in the range of about 178 to 8,888 standard cubic meters per cubic meter of charge (1,000 to 50,000 standard cubic feet (scf) per barrel of charge) preferably between about 355 to about 5,333 std. $m^3/m^3$ (2,000 and 30,000 scf per barrel of charge).

The reaction zone effluent is normally removed from the catalyst bed, subjected to partial condensation and vapor-liquid separation and then fractionated to recover the various components thereof. The hydrogen and, if desired some or all of the unconverted heavier materials, are recycled to the reactor. Alternatively, a two-stage flow may be employed with the unconverted material being passed into a second reactor. Catalysts of the subject invention may be used in just one stage of such a process or may be used in both reactor stages.

Catalytic cracking processes are preferably carried out with the catalyst composition using feedstocks such as gas oils, heavy naphthas, deasphalted crude oil residua, etc. with gasoline being the principal desired product. Temperature conditions of about 454° C. to about 593° C. (850° to 1100° F.,) LHSV values of 0.5 to 10 $hr^{-1}$ and pressure conditions of from about 0 to about 345 kPag (50 psig) are suitable.

Isomerization reactions are carried out in a temperature range of about 371° C. to about 538° C. (700-1000° F.). Olefins are preferably isomerized at temperatures of about 260° C. to about 482° C. (500° F. to 900° F.), while paraffins, naphthenes and alkyl aromatics are isomerized at temperatures of about 371° C. to 538° C. (700° F. to 1000° F.).

Hydrogen pressures are in the range of about 689 to about 3,445 kPag (100 to 500 psig). Contact times usually correspond to liquid hourly space velocities (LHSV) in the range of about 0.1 $hr^{-1}$ to 10 $hr^{-1}$. Hydrogen to hydrocarbon molar ratios in the range of 1 to 20, preferably between 4 and 12.

In a dehydrogenation process, dehydrogenatable hydrocarbons are contacted with the catalyst of the instant invention in a dehydrogenation zone maintained at dehydrogenation conditions. This contacting can be accomplished in a fixed catalyst bed system, a moving catalyst bed system, a fluidized bed system, etc., or in a batch-type operation. A fixed bed system is preferred. In this fixed bed system the hydrocarbon feed stream is preheated to the desired reaction temperature and then flowed into the dehydrogenation zone containing a fixed bed of the catalyst. The dehydrogenation zone may itself comprise one or more separate reaction zones with heating means there between to ensure that the desired reaction temperature can be maintained at the entrance to each reaction zone. The hydrocarbon may be contacted with the catalyst bed in either upward, downward or radial flow fashion. Radial flow of the hydrocarbon through the catalyst bed is preferred. The hydrocarbon may be in the liquid phase, a mixed vapor-liquid phase or the vapor phase when it contacts the catalyst. Preferably, it is in the vapor phase.

Hydrocarbons which can be dehydrogenated include hydrocarbons with 2 to 30 or more carbon atoms including paraffins, isoparaffins, alkylaromatics, naphthenes and olefins. A preferred group of hydrocarbons is the group of normal paraffins with 2 to about 30 carbon atoms. Especially preferred normal paraffins are those having 2 to 15 carbon atoms.

Dehydrogenation conditions include a temperature of from about 400° C. to about 900° C., a pressure of from about 1 to about 1013 kPa and a liquid hourly space velocity (LHSV) of from about 0.1 to about 100 $hr^{-1}$. Generally for normal paraffins the lower the molecular weight the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds.

The dehydrogenatable hydrocarbons may be admixed with a diluent material before, while or after being flowed to the dehydrogenation zone. The diluent material may be hydrogen, steam, methane, ethane, carbon dioxide, nitrogen, argon and the like or a mixture thereof. Hydrogen is the preferred diluent. Ordinarily, when hydrogen is utilized as the diluent it is utilized in amounts sufficient to ensure a hydrogen to hydrocarbon mole ratio of about 0.1:1 to about 40:1, with best results being obtained when the mole ratio range is about 1:1 to about 10:1. The diluent hydrogen stream passed to the dehydrogenation zone will typically be recycled hydrogen separated from the effluent from the dehydrogenation zone in the hydrogen separation zone.

Water or a material which decomposes at dehydrogenation conditions to form water such as an alcohol, aldehyde, ether or ketone, for example, may be added to the dehydrogenation zone, either continuously or intermittently, in an amount to provide, calculated on the basis of equivalent water, about 1 to about 20,000 weight ppm of the hydrocarbon feed stream. About 1 to about 10,000 weight ppm or water addition gives best results when dehydrogenating paraffins having from 2 to 30 or more carbon atoms.

Hydrogenation processes including selective hydrogenation of dienes and trienes can be carried out using reactors and hydrogenation zones similar to the dehydrogenation process described above. Specifically, hydrogenation conditions include pressures of about 0 kPag to about 13,789 kPag, temperatures of about 30° C. to about 280° C., $H_2$ to hydrogenatable hydrocarbon mole ratios of about 5:1 to about 0.1:1 and LHSV of about 0.1 to about 20 $hr^{-1}$.

The layered catalysts of this invention can also be used in oxidation reactions. These oxidation reactions include:

1) partial oxidation of hydrocarbon streams, such as naphtha or methane, to generate synthesis gas ($CO+H_2$);
2) selective oxidation of hydrogen produced from endothermic dehydrogenation reactions such as ethylbenzene to styrene; and,
3) oxidation of methane, ethane or carbon monoxide to clean up flue gas emissions from combustion processes.

The layered sphere catalyst will be of most benefit to processes where the activity or selectivity of the catalyst is limited by intraparticle diffusional resistance of product or reactants.

The conditions for the oxidation process depend on the individual process application but are generally about 350° C. to about 800° C., about 40 kPa to about 2030 kPa, with a diluent present in the feedstream such as $N_2$, $CO_2$, HO to control the reaction. Hydrogen may also be present as a diluent and also a reactant. For the selective oxidation of hydrogen, the molar ratio of oxygen to $H_2$ may vary from about 0.05 to about 0.5. The diluent level is generally from about 0.1 to about 10 moles of diluent per mole of hydrocarbon. For example, the steam to ethylbenzene molar ratio may be from about 5:1 to about 7:1 during the dehydrogenation of ethylbenzene. Typical space velocity for oxidation is between about 0.5 to about 50 $hr^{-1}$ LHSV.

The following examples are presented in illustration of this invention and are not intended as undue limitations on the generally broad scope of the invention as set out in the appended claims.

Example 1

A slurry was prepared by adding to a vessel 634.2 g of deionized water, 110 g of 15% of poly-vinyl alcohol (PVA) solution and 11.1 g of acetic acid. The subsequent mixture was stirred and to it there were added 221.8 g of zirconia powder followed by 272.8 g of zirconia sol binder. The resultant mixture was milled for 8 hours.

This resultant slurry was used to spray 700 g of 7 mm diameter cordierite spheres using a coating apparatus to give a layer having an average thickness of 200 micrometer. The coated spheres were unloaded from the coating chamber and heated in air up to 600° C. where they were calcined for 4 hours under dry air. The calcined spheres were tested for attrition resistance by taking 50 cc of the calcined spheres, placing them in a flat drum and rotating the drum at 25 rpm for 10 minutes. The impact breakage (IB) was determined as the weight percent fines generated versus the total weight of the spheres. The IB for this sample was found to be 17.5 wt. %.

Example 2

Into a container there were added 1,021.6 g of deionized water, 205.9 g of a 15% PVA solution and 21.2 g of acetic acid. The mixture was stirred and to it there were added 27.3 g of mullite fibers comprising 80% $Al_2O_3$, 20% $SiO_2$ with an average fiber length of about 200 micrometers and an average diameter of about 3 micrometers. Next, 426.2 g of zirconia powder was added followed by 469.8 g of zirconia sol binder. The mixture was then ballmilled for about 6 hours.

The resultant slurry from above was sprayed onto 711 g of 7 mm diameter cordierite spheres using a slurry coating apparatus to obtain wet spheres having an outer layer of about 200 micrometers thick. The wet spheres were heated in air to 600° C. and calcined at 600° C. for 4 hours under dry air. The calcined spheres were tested for impact breakage and were found to have an IB of 3.3 wt. %.

Example 3

A slurry was formed by adding 1,121.7 g of deionized water and 225.5 g of a 15% PVA solution and 23.2 g of acetic acid into a vessel. The resultant mixture was stirred and to it there were added 29.9 g of mullite fibers as described in Example 2 followed by the addition of 463.9 g of zirconia powder and then 514.5 g of zirconia sol binder. The resultant slurry was ballmilled for 6 hours.

The resultant slurry was used to deposit a layer onto 800 g of 7 mm diameter cordierite spheres using a slurry coating apparatus thereby producing wet spheres having a layer with an average thickness of about 100 micrometers. The wet spheres were calcined at 600° C. for 4 hours under dry air and were found to have an IB of 3.0 wt. %.

Example 4

Into a mixing vessel there were added 602.8 g of deionized water, 122.5 g of a 15% PVA solution and 12.6 g of acetic acid. The mixture was stirred and to it there were added 15.3 g of titania fibers having an average length of about 3 micrometers and an average diameter of about 0.3 micrometers. Next 253.7 g of zirconia powder were added followed by 279.6 g of zirconia sol binder. The resulting slurry was ballmilled for 6 hours.

The slurry described above was used to deposit a layer onto 730 g of 7 mm diameter cordierite spheres by spraying the slurry onto the spheres using a slurry coating apparatus to give wet spheres having an outer layer of with an average thickness of 200 micrometers. The wet spheres were calcined at 600° C. under dry air for 4 hours. The calcined spheres were tested and were found to have an IB of 2.0 wt. %.

Example 5

Into a mixing vessel there were added 622.1 g of deionized water, 129 g of 15% PVA solution and 13.1 g of acetic acid. The mixture was stirred and to it there were added 35.8 g of titania fibers as described in Example 4 followed by the addition of 263.8 g of zirconia powder and finally 310.4 g of zirconia sol binder. The resultant slurry was ballmilled for about 6 hours. The slurry contained approximately 10 wt. % titania fibers.

A portion of the slurry was deposited onto 730 g of 7 mm diameter cordierite spheres using a slurry coating system to give a layer having an average thickness of about 200 micrometers. The wet spheres were calcined at 600° C. for 4 hours under dry air and were found to have an IB of 1.4 wt. %.

It will be further appreciated that functions or structures of a plurality of components or steps may be combined into a single component or step, or the functions or structures of one-step or component may be split among plural steps or components. The present invention contemplates all of these combinations. Unless stated otherwise, amounts, dimensions and geometries of the various components depicted herein are not intended to be restrictive of the invention, and other amounts, dimensions or geometries are possible. It will also be appreciated from the above that the fabrication of the unique catalysts herein and the use thereof also constitute methods in accordance with the present invention. The present invention also encompasses intermediate (e.g. precatalysts) and end products resulting from the practice of the methods herein. The use of "comprising", "having", "containing" or "including" also contemplates embodiments that "consist essentially of" or "consist of" the recited feature.

The explanations and examples presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patents, patent applications and publications, are incorporated by reference for all purposes.

What is claimed is:

1. A method of producing alkenyl alkanoates, comprising:
   contacting a feed comprising an alkene, an alkanoic acid and an oxygen containing gas to a catalyst comprising a layered composition comprising:
   an inner core; and
   an outer layer comprising a refractory inorganic oxide, a fibrous component, an inorganic binder, and palladium and gold as catalytic components dispersed on the outer layer.

2. The method of claim 1 where the fibrous component comprises inorganic fibers, organic fibers or combinations thereof.

3. The method of claim 2 where the inorganic fibers comprise mullite, titania, potassium titanate, alumina, zirconia, silica, silicon carbide, cordierite, glass or combinations thereof.

4. The method of claim 2 where the organic fibers comprise graphite, carbon, polymers or combinations thereof.

5. The method of claim 1 where the inner core comprises alpha alumina, theta alumina, silicon carbide, metals, montmorillonite, cordierite, gamma alumina or combinations thereof.

6. The method of claim 5 where the inner core comprises cordierite.

7. The method of claim 1 where the outer refractory inorganic oxide comprises gamma alumina, delta alumina, eta alumina, theta alumina, silica/alumina, zeolites, nonzeolitic molecular sieves, titania, zirconia, niobia or combinations thereof.

8. The method of claim 7 where the outer layer comprises zirconia.

9. The method of claim 1 where the inorganic binder comprises alumina, silica, zirconia, titania, aluminum phosphate or combinations thereof.

10. The method of claim 1 where the layered composition has an impact breakage of less than about 10 wt. %.

11. The method of claim 10 where the layered composition has an impact breakage of less than about 5 wt. %.

12. The method of claim 11 where the layered composition has an impact breakage of less than about 3 wt. %.

13. The method of claim 1 wherein the layered composition further comprises a promoter component dispersed on the outer layer, where the promoter component comprises an alkali metal.

14. The method of claim 1 wherein the layered composition further comprises an organic bonding agent.

15. The method of claim 14 where the organic bonding agent comprises polyvinyl alcohol (PVA), hydroxyl propyl cellulose, methyl cellulose, carboxy methylcellulose or combinations thereof.

16. The method of claim 1 where the outer layer has deposited thereon from one to about 5 additional layers and where adjacent layers comprise different inorganic oxides.

17. The method of claim 1 where the inner core has a lower capacity for catalytic components relative to the outer layer.

18. The method of claim 1 wherein the alkene is ethylene, the alkanoic acid is acetic acid and the oxidizer is an oxygen containing gas.

19. The method of claim 18 where the catalyst comprises between about 1 to about 10 grams of palladium, and about 0.5 to about 10 grams of gold per liter of catalyst, with the amount of gold being from about 10 to about 125 wt % based on the weight of palladium.

20. The method of claim 19 where the catalyst further comprises a potassium containing promoter component dispersed on the outer layer in an amount between about 10 and about 70 grams per liter of catalyst.

21. The method of claim 1 where the inner core comprises cordierite and the outer layer comprises zirconia.

22. The method of claim 21 wherein the inorganic fiber comprise titania.

23. The method of claim 1 wherein the fibrous component is dispersed throughout the outer layer.

* * * * *